(12) United States Patent
Bates

(10) Patent No.: US 11,389,135 B2
(45) Date of Patent: Jul. 19, 2022

(54) BREAST IMAGING ULTRASOUND SYSTEMS AND METHODS

(71) Applicant: Estate of Kenneth N. Bates, Portland, OR (US)

(72) Inventor: Kenneth N. Bates, Portland, OR (US)

(73) Assignee: Cassandra L. Bates, Northborough, MA (US)

( * ) Notice: Subject to any disclaimer, the term of this patent is extended or adjusted under 35 U.S.C. 154(b) by 0 days.

(21) Appl. No.: 16/911,396

(22) Filed: Jun. 25, 2020

(65) Prior Publication Data
US 2020/0405260 A1    Dec. 31, 2020

Related U.S. Application Data

(60) Provisional application No. 62/867,664, filed on Jun. 27, 2019.

(51) Int. Cl.
| | |
|---|---|
| *A61B 8/00* | (2006.01) |
| *A61B 8/08* | (2006.01) |
| *B06B 1/06* | (2006.01) |

(52) U.S. Cl.
CPC ............ *A61B 8/406* (2013.01); *A61B 8/0825* (2013.01); *A61B 8/4272* (2013.01); *A61B 8/4461* (2013.01); *A61B 8/4477* (2013.01); *A61B 8/4488* (2013.01); *A61B 8/483* (2013.01); *A61B 8/5207* (2013.01); *B06B 1/0625* (2013.01)

(58) Field of Classification Search
CPC .. A61B 8/00; A61B 8/08; A61B 8/406; A61B 8/0825; A61B 8/427; A61B 8/4461; A61B 8/4477; A61B 8/4488; A61B 8/483; A61B 8/5207; A61B 8/0625
See application file for complete search history.

(56) References Cited

U.S. PATENT DOCUMENTS

| | | | |
|---|---|---|---|
| 2003/0163046 A1* | 8/2003 | Nohara | G01S 15/8993 600/443 |
| 2003/0220569 A1 | 11/2003 | Dione et al. | |
| 2004/0050166 A1 | 3/2004 | Batzinger et al. | |
| 2004/0064046 A1 | 4/2004 | Shehada | |
| 2004/0249283 A1 | 12/2004 | Kantorovich et al. | |
| 2009/0259128 A1* | 10/2009 | Stribling | A61B 8/445 600/459 |

(Continued)

FOREIGN PATENT DOCUMENTS

WO    WO-0217792 A1 *   3/2002   ......... A61B 8/0825

OTHER PUBLICATIONS

Harris, Nick and Y. Qian. "Design of a high frequency equal width annular array transducer for medical imaging." (2013).*
(Continued)

*Primary Examiner* — Carolyn A Pehlke
(74) *Attorney, Agent, or Firm* — File-EE-Patents.com; Jay A. Chesavage

(57) ABSTRACT

A breast imaging ultrasound system for ultrasound imaging of a body includes: scanning uniform sub-volumes of a mammalian breast with an ultrasound transducer having a fixed focal number (FN), acquiring ultrasonic images of portions of the target volume, the acquired images having the same voxel resolution, and processing the ultrasonic images, thereafter providing a 2D or 3D image of the target volume using constant size volume pixels (Voxels).

3 Claims, 9 Drawing Sheets

(56) References Cited

U.S. PATENT DOCUMENTS

| | | | |
|---|---|---|---|
| 2010/0022921 A1 | 1/2010 | Seip et al. | |
| 2017/0164915 A1* | 6/2017 | Li et al. | |
| 2017/0238908 A1* | 8/2017 | Hisatsu | A61B 8/5207 |
| 2018/0100832 A1* | 4/2018 | Ebisawa | G01N 29/223 |
| 2018/0161014 A1* | 6/2018 | Wu | A61B 8/15 |
| 2020/0008784 A1* | 1/2020 | Yamanaka | A61B 8/4477 |

OTHER PUBLICATIONS

Chabok, H. R., Cannata, J. M., Kim, H. H., Williams, J. A., Park, J., & Shung, K. K. (2011). A high-frequency annular-array transducer using an interdigital bonded 1-3 composite. IEEE transactions on ultrasonics, ferroelectrics, and frequency control, 58(1), 206-214.*

Dietz, D. R., S. I. Parks, and M. Linzer. "Expanding-aperture annular array." Ultrasonic imaging 1, No. 1 (1979): 56-75.*

Yao (ultrasound lecture 2, https://eeweb.engineering.nyu.edu/~yao/EL5823/Ultrasound_Lecture2_F16.pdf, Nov. 5, 2016).*

\* cited by examiner equal width transducer

Front · Side equal width half transducer

Front · Side

Constant F number aperture

Annular Array with Acoustic Lens equal area transducer
Prior Art

Beam Profile vs Z

Section A-A

BREAST IMAGING ULTRASOUND SYSTEMS AND METHODS

The present invention claims priority to U.S. Pat. App. 62/867,664 filed Jun. 27, 2019.

FIELD OF THE INVENTION

The present invention relates to a diagnostic imaging system. In particular, the invention relates to an ultrasound system for diagnosis of diseased breast tissue.

BACKGROUND OF THE INVENTION

X-ray mammography is the recognized breast cancer screening technology. Unfortunately, this technology misses many breast cancers in women with radiologically dense breasts. This is a significant problem as it affects approximately 40% of all women in the United States. Furthermore, X-Ray systems expose patients to harmful radiation and are extremely uncomfortable for patients due to significant compression of the breast. Patient comfort is actually a medically important issue as the pain of compression is the reason a significant percentage of women will not continue with mammographic checkups after their first exam. The growing awareness of these limitations of X-ray mammography has dramatically increased the number of women undergoing supplemental diagnostic methods such as medical ultrasound and MRI.

Due to their high resolution and 3D imaging capability, MRI systems are effective but are very expensive both in capital outlay and maintenance.

Traditional ultrasound systems are significantly less expensive but are diagnostically limited due to operator dependency as well as fundamental design limitations. This, in turn, has propelled the demand for dedicated breast imaging ultrasound systems, particularly those systems that automate the breast screening process known as ABUS (Automated Breast Ultrasound Screening).

Currently, there are two fundamental types of ABUS systems, those that automate the traditional ultrasonic imaging technology such as B-scan (a cross section planar ultrasound scan, typically an ultrasound transducer dynamically focused in one axis and scanning in the other axis to produce a planar image), and systems that perform ultrasound tomography (3D imaging) using thousands of individual transducers and require significant computation. All use some form of physical motion of the ultrasonic transducers.

The ABUS systems that automate the current B-scan ultrasound technology have less resolution than MRI, compress the breast, are time consuming to clean between patients, and are more expensive than the human operated systems they are designed to replace. The computationally extensive ultrasound tomographic ABUS systems provide excellent images but are difficult to clean and extremely expensive.

An additional issue with the prior art ultrasound systems is comfort to the patient. One prior art ABUS system only slightly compresses the breast as a probe of a conventional ultrasound system is moved around the breast. It provides a 3D image via the use of a 3D tracking system that monitors the position of the probe. Some compression, i.e. breast distortion, is inevitable due to the need for physical contact between the breast and the acoustic probe. The ABUS Sofia® (a trademark owned by iVu Imaging Corporation) also compresses the breast somewhat due to the need for its probes to contact the breast as they are scanned in a rotary motion. Systems such as SoftVue® (a trademark owned by Delphinus Medical Technologies, Inc), do not compress the breast as they use a water bath for breast imaging.

Additionally, many of the prior art ABUS systems are time consuming to clean between patients. Such cleaning is needed to prevent possible cross-contamination between patients. In the case of those systems that move the transducer over the breast either in direct contact such as Hitachi or through an acoustically transparent mesh such as GE and Siemens, a large amount of acoustic couplant is used to ensure an acoustic path between the transducer probe and the breast. This requires time for the patient to remove the couplant from the breast and time to remove the couplant from the acoustic probe and portions of the scanning mechanism. Certain prior art ABUS systems must be cleaned as well but due to the small size of the transducer probe, cleaning is faster. For those systems that use a water bath to couple the acoustic energy from the transducer array/s to the breast, they also require a significant time to clean. For these systems, the water needs to be drained and the entire inside of the water tank and scanning mechanism must be wiped with a sterilizing and/or cleaning solution to remove any pathogens or contaminants left over from the previous patient.

It is desired to provide an ultrasound imaging system suitable for breast imaging that provides constant 3D spatial resolution and constant sized image voxels to provide consistent imaging throughout the entire volume of the breast while using a small number of individual transducers or alternatively an array of transducers, and it is desired that this system be suitable for use with mechanical transducer beam steering and/or electrical transducer beam focusing.

Objects of the Invention

A first object of the invention is an ultrasound system providing constant 3D spatial resolution and constant sized voxel images comprising an annular array transducer having equal width rings, the equal width rings selected in groups during transmit to form transmit region (each region being an axial range of focus where the beam diameter is limited to no greater than ½ that of the minimum beam diameter), and equal width rings selected in groups of one or more rings during receive to maintain constant spatial resolution also limited to no greater than the minimum beam diameter over a range of depths greater than allowable using an annular array transducer having equal area rings.

A second object of the invention is an ultrasound system providing simultaneous scanning of a plurality of imaged regions and adjacent regions, the system comprising a plurality of independently rotatable supports on parallel axis, the independently rotatable supports surrounded by a water bath, the rotatable supports individually rotating about the plurality of imaged regions.

A third object of the invention is an imaging system comprising a water bath, a rotatable support which includes one or more ultrasound transducers which may be annular arrays of equal ring width, the rotatable support optionally adjustable for height along an axis of rotation, the ultrasound transducer acquiring reflected or transmitted ultrasound energy from tissue volumes of substantially equal volume and dimension.

A fourth object of the invention is an imaging system comprising a water bath, a rotatable support mechanically coupled to at least one ultrasound transducer such as an equal ring width annular array, the ultrasound transducer operative to encircle a human breast, the imaging system also having ancillary transducers for imaging regions adjacent to the human breast, the imaging system optionally operative to detect spiculated masses in the human breast and surrounding tissues.

A fifth object of the invention is a method for detection of breast cancer, the method comprising:

acquiring uniform 3D spatial resolution ultrasound acoustic energy reflections and a constant size voxel image of a region, detecting a suspected lesion in at least one sub-region of interest by comparison of the structure of the suspected lesion to a series of templates, the system thereafter acquiring a higher resolution image using smaller 3D spatial resolution acquisition in at least one region of interest.

SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter. A key aspect of the system is providing images with constant 3D resolution and constant voxel images by the use of a constant width annular ring transducer for ultrasound transmission and reception, or alternatively a linear array which is mechanically scanned to acquire imaged voxels in a particular region of focus such that all acquired imaged voxels have substantially uniform dimensions.

Prior art examples of imaging systems which provide constant 3D spatial resolution and constant voxel images include Magnetic Resonance Imaging (MRI) and X-Ray Computerized Axial Tomography (CT). MRI systems are large, expensive, and unsuitable for portable in-office use. X-Ray CT is similarly large, expensive, and non-portable, so is rarely used for follow-up imaging.

Currently, prior art ultrasonic reflection ultrasonic imaging use electronic dynamic focusing in the in one dimension perpendicular to the ultrasound beam axis and an acoustic lens to focus the acoustic signals in the other perpendicular dimension to the beam axis. This inherently results in the 3D spatial resolution of these systems changing with depth, which will cause a pathology of interest to have a depth dependent appearance, and it becomes more difficult to distinguish diseased tissue from surrounding healthy tissue because of the change in resolution. Even those systems that use a 2D acoustic electronically focused transducer array (the surface of the ultrasound transducer steerable on two orthogonal axis) have a 3D spatial resolution that changes with depth once a specific range is exceeded. These 2D array technologies can, in principle, achieve constant 3D spatial resolution, but only through a dramatic increase in complexity and cost.

The present invention achieves constant 3D spatial resolution through the use of a constant F# (focal length divided by the aperture, also referred to as a focal number) acoustic focus and the limitation of the acquired acoustic data to be used to produce the image to a small region around and including the focus. In some embodiments, the target F# (also referred to as a focal number or FN) is between 1.5 and 2.5 and the acoustic data region is limited to no more than $+/-S*\lambda*F\#^2$ (eq. 1) about the focus. S is an arbitrary parameter between 0.5 and 2.5 and $\lambda$ is the acoustic wavelength in the breast tissue over frequency ranges between 1 MHz and 20 MHz.

The present invention provides a constant F#, which can be achieved in a number of ways. One method is the use of a specially designed annular array whose active aperture is changed in direct proportion to the focus to keep the F# constant. Another method replaces the annular array with a ring of single element transducers each having a different focus but the same F. A single transducer with a focal length corresponding to the center of the scanning mechanism and a fixed F# can be used along with a scanning assembly that mechanically moves the transducer radially during the scan.

In another example of the invention, only a small acoustic data region around the focus of the transducer is used to maintain a substantially constant 3D spatial dimension over depth. This region is identified as the incremental scan depth. The lateral dimensions of this region are determined by the acoustic frequency and the F. Since both are fixed, the lateral spatial dimension (orthogonal to the beam axis) in this region is constant. The depth resolution is determined by the bandwidth of the transducer and associated electronics. Since the bandwidth is to be held constant, so is the depth spatial resolution. Setting the acoustic data depth region, as previously described, along the axis of the transducer/s determines the region of constant 3D resolution within a given incremental scan depth. Such use of an incremental scan depth allows a decreased 3D scan time as the number of depth increments can be reduced while keeping the number of constant sized image voxels constant. The incremental scan depth is broken into these image voxels electronically in the receive electronics or algorithmically in the computer used to create the final image using the collected acoustic data. It is understood in the present context that an image voxel represents the image formed from the acquired data, in other descriptions, the image voxel may be understood to refer to the acquired data itself.

The mechanical scanning mechanism of the inventive technology is responsible for rotating the transducer/s in a circle around the breast as well as in a vertical axis that contains the center of the scanning circle. This motion provides two, angular and axial, of the three axes required for 3D imaging. The third, radial axis, is covered by the acoustic scanning of the annular array, a sequence of multiple single element focused transducers, or a mechanical mechanism for moving a single element focused transducer. In the preferred embodiment, continuous rotary motion is desired to allow for faster scanning and lower mechanical hydrodynamic forces than a system where the rotary motion alternated between 360 degrees in one direction and then reverses for 360 degrees or a system where the rotary motion is incremental. The 3D scan time can be proportionally reduced by using additional constant F# single element transducers and/or 2D phased arrays and associated electronics. An additional value of this scanning mechanism is the ability to incorporate other imaging technologies such as photoacoustic, infrared, microwave, X-ray, etc.

In the case of the single element transducer, the physical placement of each substantially constant 3D spatial resolution region is achieved with mechanical motion in three orthogonal dimensions. For the linear sequence of individually focused transducers, the placement of each substantially constant 3D spatial resolution region is determined angularly and radially by a combination of the rotation of the transducer assembly, and placement of each transducer in the transducer ring. Placement in the axial dimension is determined by the vertical placement of the ring. In one embodiment, using a specially designed annular array, the placement along the radius is determined electronically by beamforming electronics known in the art and the angular and axial placement is determined mechanically. Given that only the acoustic signals around the focus of each transmit cycle are used, the associated transducer electronics can be multiplexed between transducers thereby reducing the amount of electronics required.

The substantially constant 3D spatial resolution region placements need not be spatially unique. Some overlap in the placement of these regions may contribute to improved image quality. In one embodiment, this overlap should not exceed more than 2 spatial resolution increment in the radial or angular dimensions nor more than 5 in axial. The spatial increments can be collected in any scanning format consistent with a cylindrical or spherical co-ordinate system.

There is clinical value in imaging as close to the chest wall as possible. With a simple vertical translation of the transducer, this cannot be achieved with a large circular aperture transducer as the closest image acquisition possible is ½ the vertical width of the transducer (the radius of a circular aperture). However, a slight degradation of the spatial resolution is acceptable for the purposes of imaging close to the chest wall. Reducing the transducer aperture in elevation down to the axis achieves this goal. Thus, a circular aperture transducer becomes a semi-circular one. This allows the axis of the transducer to be placed close to the chest wall as possible and so allow the image to be as close to the chest wall as possible.

In one embodiment of the scanning mechanism, the electronics used for transmitting and receiving the acoustic signals are contained within the rotating assembly and these signals, timing and control are linked with the rest of the imaging system through one or more RF links. This greatly decreases the transference of such signals that would otherwise require rotating electronic connections. A further refinement would be to power the electronics though RF and/or magnetic field/s.

Another feature of the inventive technology is that the breast is not compressed. Most of the Automated Breast Ultrasound (ABUS) systems currently on the market compress the breast to reduce the distance through which an image is made. Unlike X-ray mammography, these systems compress the breast towards the body. They are still somewhat uncomfortable for the patient albeit less so than standard X-ray mammography.

The inventive technology may use two water tanks, one that contains the acoustic transducers and scanning assembly and a smaller tank that is placed between the transducers and scanning assembly and the breast. The inner tank is fabricated from an acoustically transparent, or nearly transparent (e.g., low acoustic absorption (absorbing less than of the acoustic energy) and an acoustic impedance close to the couplant fluid material (within 5%) and, preferably, has a wall thickness no more than 10% greater than and no less than the axial spatial resolution increment of the system. Alternatively, the wall thickness may be less than ¼ a wavelength of propagating ultrasound energy. Furthermore, it is preferable that the spacing between the inner wall and the surface of the acoustic transducer/s should also be no more than 10% greater than and no less than the axial spatial resolution increment of the system or, alternatively, less than ¼ of a wavelength of propagating ultrasound energy.

Having a wall thickness greater than the incremental scan depth ensure that acoustic reflections from the inner and outer surfaces of the inner tank will be proportionally separated in time from the acoustic signal contained within the incremental scan depth. This greatly simplifies the echo cancellation, by means known in the art, of the earlier acoustic reflections from the inner and outer surfaces of the inner tank. This is also true for the spacing between the transducer surface and the inner wall. The embodiments of the present technology are much easier to clean as only the inside of the inner tank needs to be cleaned. Furthermore, the inner tank can be constructed to provide a safety barrier between the moving components and the patient's breast. To save even more time, the inner tank can be a removable item. In this case, the inner tank can be either disposed or refurbished.

To ensure the highest quality images, the transducers' focus may be shaped to reduce or compensate for the distortion caused by the inner tank. In one example of the invention, the distortion of a cylindrical tank can be reduced by a converse cylindrical shaping of the transducer surface to correct for cylindrical lens effects that can be generated by such an inner tank. This may also be accomplished by an appropriately shaped acoustic lens in front of the transducer. In yet in another example of the invention, the distortion can be reduced by making the inner tank wall thickness less than ¼ an acoustic wavelength being propagated while keeping the speed of sound of the couplant in the inner tank within 10% of that in the outer tank. In another example, by providing the inner tank wall with a material which has a speed of sound which is within 10% of the couplant speed of sound in both tanks, the distortion can be reduced.

As an example of focus correction in a cylindrically shaped inner tank, the transducers' focus is shaped in such a way to correct for the induced cylindrical distortion. In the best embodiment, the cylindrical distortion is corrected by the addition of an appropriate cylindrical curvature lens in front of the transducer. This distortion may also be corrected by the addition of an appropriate cylindrical curvature to the transducers' transmit/receiving surface.

BRIEF DESCRIPTION OF THE DRAWINGS

FIG. 2F-1 shows a beam plot in the x-z direction.

FIG. 2F-2 shows a beam plot in the y-z direction

FIG. 2F-3 shows a beam profile in the x-y direction.

FIG. 3 shows an imaging system which encircles the tissue to be imaged with transducers.

DETAILED DESCRIPTION OF THE INVENTION

Figure 1:
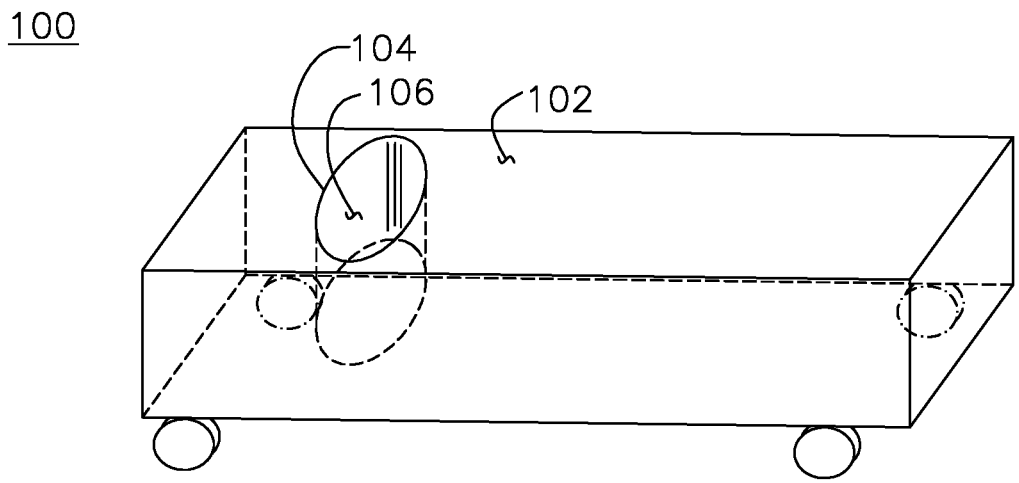
FIG. 1 is an example perspective view of a breast imaging system.

FIG. 1 shows an example scanning system table 102 with opening 104 and aperture 106 for placement of one or more breasts to be scanned. The scanning system consists of a table 102 along with an operator's console (not shown) for control of the system and presentation of images. The table 102 has a padded surface with opening cavity 106 suitable for comfortable placement of the breast or breasts to be imaged. In operation, the technician guides the patient onto the table and helps ensure that the breast fits comfortably into the opening. The imaging system includes an acoustic fluid coupling tank 106 set just below or at opening 104. As bubbles in the water or couplant produce unwanted reflections that reduce the propagating power needed for imaging deeper structures, and the acoustic couplant (such as water) is in contact with the patient, the tank 106 is filled with degassed and preferably warm and sterilized water or couplant, and an initial short scan is initiated by the technician to ensure proper breast placement. Once placement is verified the technician initiates the scan which takes approximately 5 minutes or less depending on the image volume. After the scan is completed, the process is repeated for the other breast.

Figure 2:
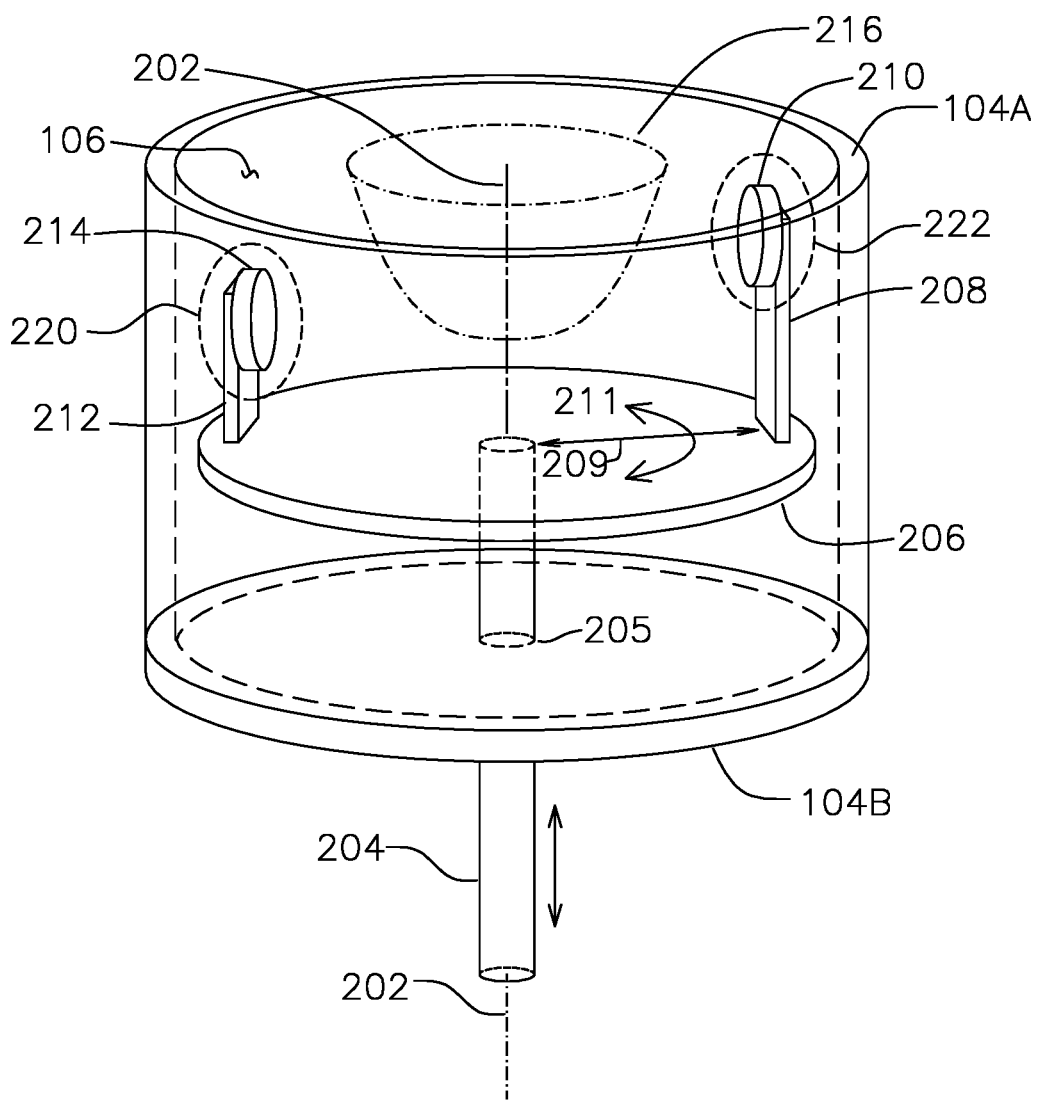
FIG. 2 is a perspective view of a first example of an imaging system having a rotational axis, translation axis and one or more ultrasound transducers.

FIG. 2 shows aspects of the imaging system, including water tank 106, a rotary support mechanism 206 that is capable of rotation about axis 202 and vertical translation along the axis 202, the rotary support mechanism 206 including one or more affordances 208, 212 for attachment of at least one 2D acoustic transducer such as 210 or 214. The transducers 210 or 214 are generally oriented to provide a focused beam directed toward the axis 202 and have sufficient penetration depth to image breast 216 when present. A human breast 216 is suspended in the center of the water filled tank 106.

Several different modes of operation are possible. In a first mode of operation, the one or more transducers 210 and/or 214 are rotated around the breast while the associated electronics both transmit and receive acoustic information to/from the breast. This configuration provides a coronal acoustic reflection image slice of the breast. In a second mode of operation, multiple coronal slices are taken by translating the transducer/s up and down the vertical axis 202 of the tank with reference to the breast being imaged using the first mode of operation. In a third mode of operation, the transducer provides a constant F# with depth, and scans are taken as a series of linear scans by translation of the transducers on axis 202, and a set of such linear scans are taken by rotating the rotary support mechanism 206 a fixed or variable angle between each linear scan. In each mode of operation, whether by mechanical means, or by electrical means (expanding the aperture to maintain F# with depth), the acquired 3D spatial resolution is maintained constant through the volume of the tissue.

The transducers 210 and 214 may operate in a wide variety of configurations, where the primary objective of the transducer configuration is to provide constant 3D spatial resolution over the region being imaged.

In the present application, the reference axis x and y refer to the dimensions of a rectangular transducer across its surface, with the x dimension indicating the longer dimension and the y dimension in dictating the shorter dimension. The direction of acoustic propagation is referred to as the z axis, generally perpendicular to the transducer surface, unless steered electronically of angle by as much as 60 degrees from perpendicular. Circular transducers may be referenced with respect to diameter D of the surface which is generally perpendicular to the direction of acoustic wave propagation. The usable axial imaging region refers to an imaged region separated from the surface of the transducer and maintaining the x and y coordinate directions for reference to the surface of the transducer.

Additionally, the present invention determines a region of interest and acquires acoustic transducer data for imaging over a relatively small sample of the acoustic signal in the range of focus of the 2D transducer/s 210 and/or 214. The 2D transducers 210 and/or 214 are either an array of focused transducers with each focus at a different depth or an annular array with the electronics creating a sequence of foci, as will be described for the series of FIGS. 2A-2E describing transducer types which may be used for 210 or 214. The present transducer arrangement provides constant 3D spatial resolution image acquisition, which provides advantages over commercial ABUS systems which utilize a 1D array of piezoelectric transducers which collect a line of acoustic image from a single transmit focus. As is known in the prior art, the spatial resolution of a rectangular (active) aperture transducer which has unequal x and y dimensions over its surface has inherently unequal spatial resolutions in each dimension in the region being sampled. In general, the spatial resolution of a transducer in the plane perpendicular to the direction of propagation is best in its longest (first) dimension and comparatively poor in its shorter (second) dimension. In these systems, the second dimension resolution may be improved by a fixed focus acoustic lens. As a result, these systems provide a high spatial contrast and high lateral resolution only in the focal region of the acoustic lens and less 3D spatial resolution elsewhere. As described by this invention, only using the small focal region, both in transmit and receive, around each transducer depth of focus, high contrast and high resolution are obtained throughout each coronal slice. High contrast resolution can be achieved by increasing the dynamic range of the acoustic signal by averaging multiple acquisitions as a function of depth. High contrast and high resolution allow for a more diagnostically relevant acoustic image including the ability to better image microcalcifications.

Prior art 2D acoustic arrays (a transducer with individual elements across its face in both x and y directions, allowing beam steering in both x and y directions) were developed but again, for real time imaging, only a fixed transmit focus could be used. A number of prior art systems allowed for a small number of transmit foci in the range of 5-6 zones, but only at the expense of image frame rate. The present system is directed to 1D arrays which provide constant 3D spatial resolution imaging in the form of either a linear/phased array with elements electrically excited to focus at one range (the focus of the acoustic lens), or an annular array where the elements are electrically excited radially. Prior art systems which provide constant 3D spatial resolution imaging over depth use 2D arrays (a rectangular array of elements which can be focused in two dimensions to maintain beam profile). For systems with n elements in a particular direction, a rectangular 2D n×n array requires $n^2$ individual signal processing delays, whereas applicant's 1D system complexity grows at a rate of n. Consequently, due to the dramatic increase in complexity and costs of 2D array systems, they are only used in the most demanding clinical situations and at depths less than would be normally be seen in the breast.

For breast imaging, the imaging requirement is for high image quality rather than real time or low frame rate. This allows for use of long image acquisition time imaging techniques such as the inventive technology. The present system provides improved breast imaging results over traditional ultrasonic breast imaging systems. The present system provides a slice imaging time on the order of 2 seconds. An example imaging time for a 10 cm long breast with 1 mm slice spacing would be 200 seconds or 3.33 minutes per breast scan. This timeframe assumes that each spatial placement of the focus is 1 mm in all directions from its neighbors. This timeframe can be halved if two sets of transducers are used for each placement cycle. Likewise, the spatial placement of the focus data spacing can be reduced to ½ mm×½ mm×1 mm position at a slice spacing of 1 mm for the same total breast image acquisition time.

Mechanical Scanning Mechanism

The mechanical scanning mechanism of FIG. 2 may be realized using many different embodiments, but the example mechanism is responsible for rotating the transducers 210 and/or 214 circularly around the breast 216 (or axis 202) as well as translating on vertical axis 202 that contains the center of the scanning circle. This motion provides two of the three axes required for 3D imaging. The third (z axis of transducers 210 and/or 214) is provided by the system electronics which provide time of flight amplitude response and also provide electronic focusing of the transducers 210/214 to maintain constant 3D spatial resolution of the acoustic beam provided by the annular array such as by sequencing the use of multiple single element focused transducers to provide a constant F#. Continuous rotary motion about axis 202 is desired to allow for faster scanning and lower mechanical hydrodynamic forces than a system where the rotary motion reverses rotational direction.

As shown in FIG. 2, an example implementation has one or more annular arrays 210 and 214 mounted on posts 208 and 212 connected to support base 206. At the center bottom of this base is a shaft 204 that goes through a rotary and linear motion seal 205 that is at the center base of the outer water tank. Rotary and linear motion of the shaft is controlled by a conventional servo-mechanical system outside the outer water tank (not shown).

Figure 2A:
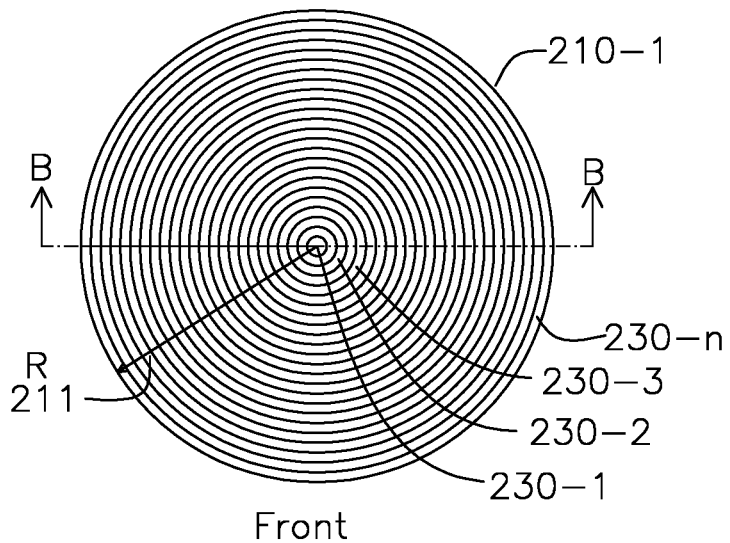
FIG. 2A shows an example transducer for use with FIG. 2, the transducer providing a constant F.
Figure 2A:
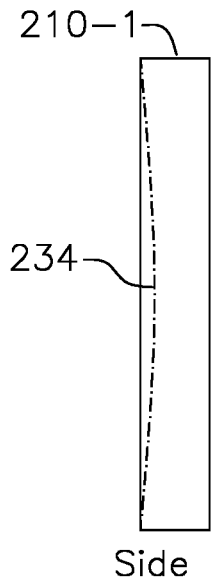
Figure 2B:
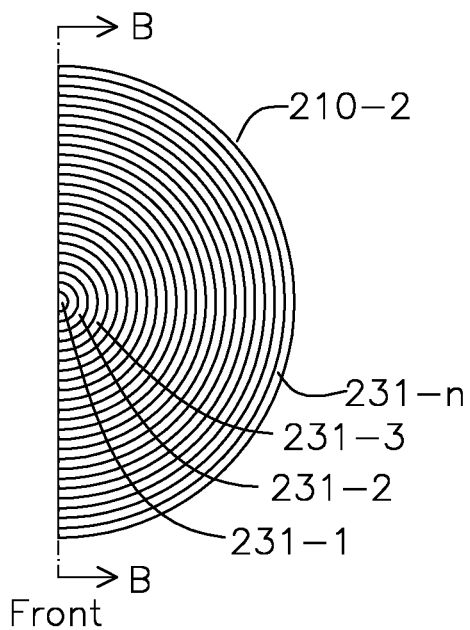
FIG. 2B shows another example transducer for use with FIG. 2.
Figure 2B:
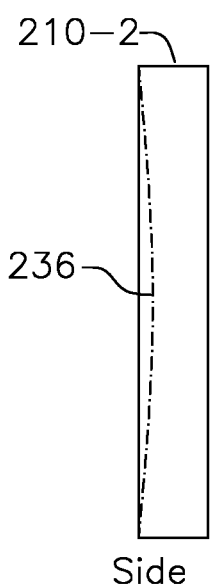
Figure 2C:
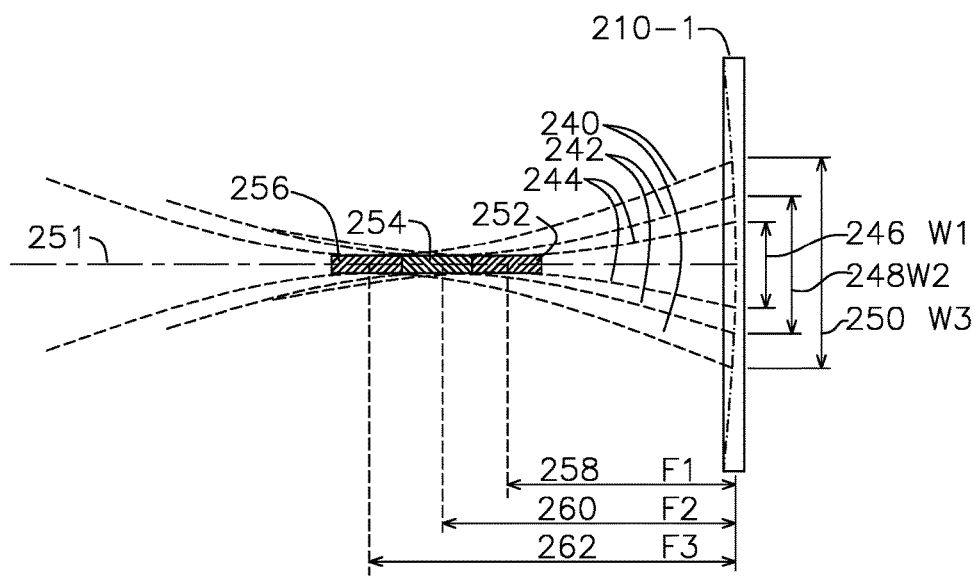
FIG. 2C shows a beam plot for a transducer having uniform F.
Figure 2D:
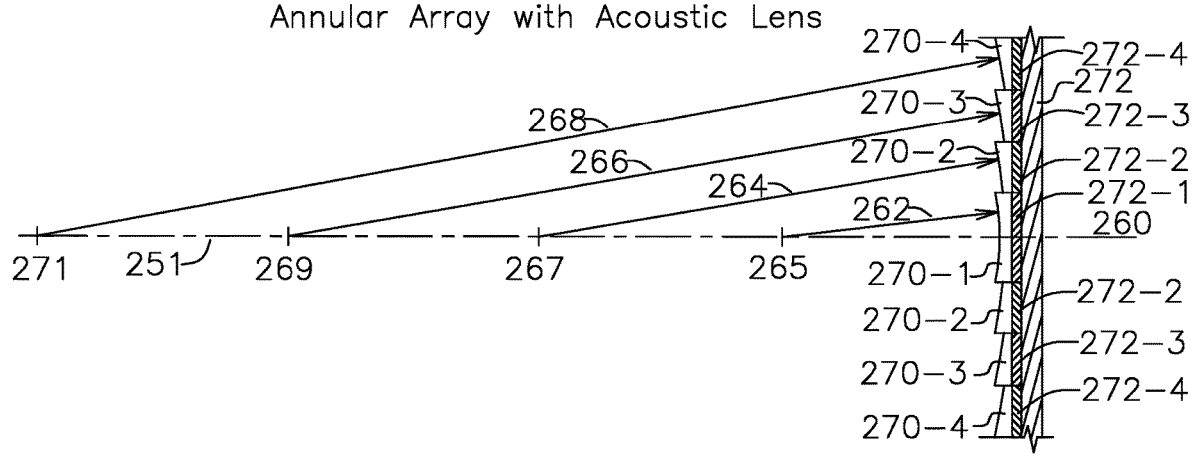
FIG. 2D shows the construction of an acoustic Fresnel lens for providing a transducer having a constant F.
Figure 2E:
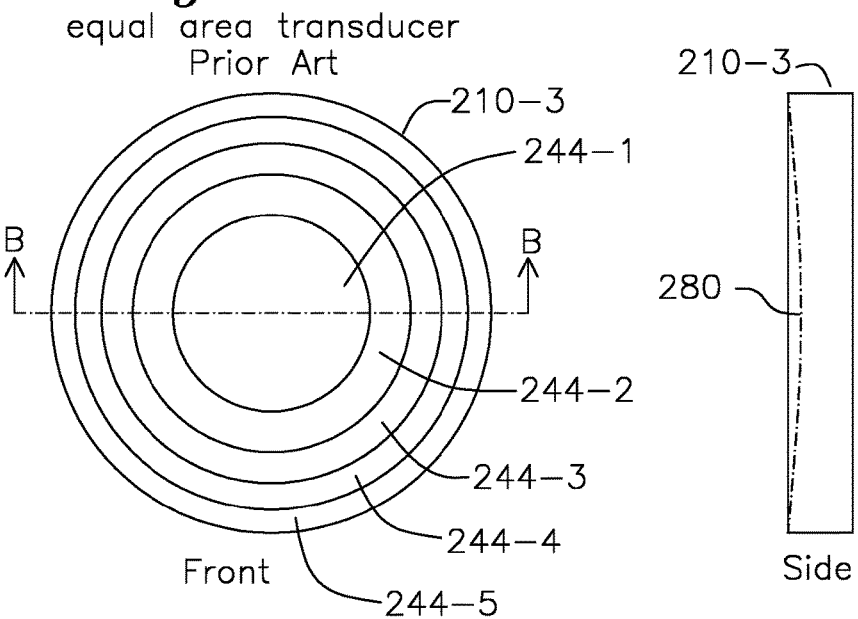
FIG. 2E shows a prior art equal area annular ring transducer.
Figure 2F:
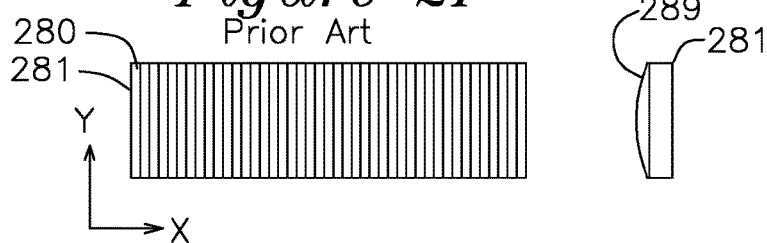
FIG. 2F shows a prior art rectangular array transducer.
Figures 1, 2F:
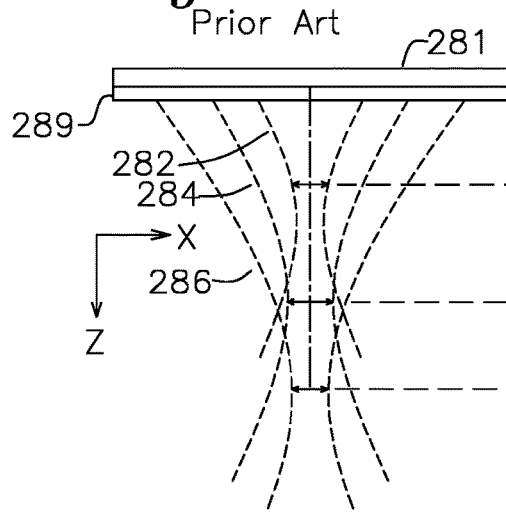
Figures 2, 2F:
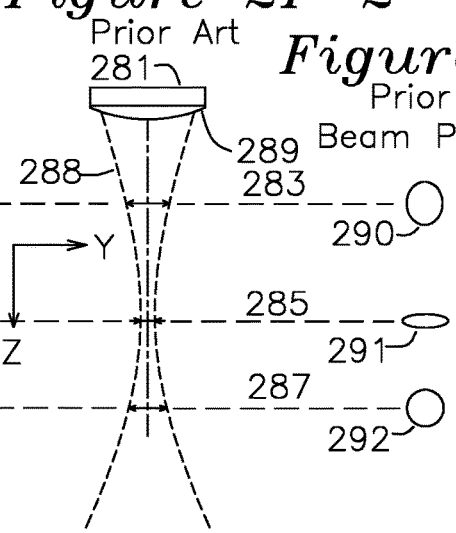
Figures 2, 2F, 3:
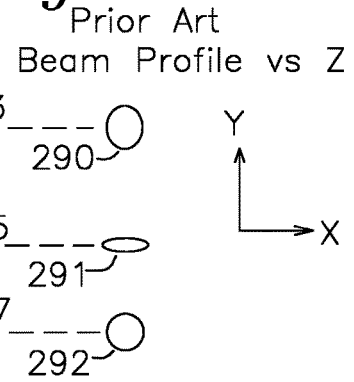

FIGS. 2F, 2F-1, 2F-2, and 2F-3 show the problem of prior art systems, and rectangular array systems in particular. FIG. 2F shows an example array transducer 281 with a plurality of individual elements 281 with respect to an x-y coordinate system (with z axis perpendicular to the view) and an acoustic lens 289 for elevation (Y dimension) focus. FIG. 2F-1 shows a beam plot in the x-z plane, with beam plots 282, 284, and 286 for various depths, such as may be accomplished by dynamic focusing or by phase focus on transmit. FIG. 2F-2 shows the beam plot 288 for transducer 281 in the y-z plane, and FIG. 2F-3 shows the beam profiles 290, 291, 292 in the x-y plane for example depths 283, 285, 287. Examination of the beam profiles 290, 291, 292 reveal the problem of using rectangular focused arrays, since the enclosed area and dimensions vary over the z extent. The range (Z dimension) spatial resolution of an imaging system is limited by the fractional bandwidth of the transducer. The image voxel resolution in that dimension is controlled by the image point sample interval, so an increased sample interval increases the voxel size in the z direction so to keep the same voxel size throughout the 3D image, the sample interval in the z direction should be constant.

Constant Ring Width Annular Array

Several different examples of ultrasound transducers 210 and 214 may be used, and the transducers 210/214 may be rectangular arrays with well controlled beam profiles, rotatable arrays, or any transducer type which provides constant voxel dimension over the imaging range of interest when imaging. FIG. 2A shows one example of the ultrasound transducer 210 or 214 as an annular array 210-1 having constant width elements 230-1, 230-2, 230-3 through 230-n, as well as a cross section view showing an optional concave surface 234. The annular array transducer 210-1 is unique due its use of constant width annular rings rather than traditional constant area annular rings of the prior art shown in FIG. 2E, where the center element 244-1 and each annular ring 244-2, 244-3, 244-4, 244-5 have equal area. The equal area annular array transducer 210-3 has been preferred in the prior art because each element has the same electrical impedance and phase errors. The advantage of an annular array with constant width rings of FIG. 2A is the ability to grow the active aperture proportional to acoustic depth thereby keeping a constant F# and resulting constant resolution. FIG. 2C shows the advantage of the array of FIG. 2A, where the use of only inner elements of extent 246 W1 naturally focus about distance 258 F1, and the use of additional inner elements of 248 W2 result in beam plot 242 which focuses over extent 260, and the use of additional outer elements of extent 250 W3 results in a focus over extent 262. By expanding the number of elements of the array, separate spatial regions 252, 254, and 256 may be sampled. Since the return acoustic signal is sampled, the volumes 252, 254, and 256 may be sampled at a constant rate which provides multiple constant voxels in each focal region 252, 254, 256.

The F# of FIG. 2C can be maintained constant by maintaining the ratio focal distance to aperture diameter (including only active elements) constant, such that of F1/W1=F2/W2=F3/W3 (for an example 3 regions, each representing a range of focus). This may be done during transmit, during receive, or both, so as to create the same focal region for each transmit/receive cycle to preserve the uniformity of voxel dimension on each acquisition. In one example of the invention, the transducer transmits using the annular ring elements within W1 246 for reception over extent 258 F1 using the same set of elements used during transmit. Transmit elements 248 W2 and 250 W3 may be used during respective separate intervals to acquire reflected acoustic energy from extent 260 and 262, respectively, and receiving on elements 248 W2 and 250 W3, respectively. Alternatively, transmission may be performed using one subset of elements, and the annular array expanded element by element during the receive interval to maintain a constant F# and create a receive beamform which is uniform over depth. One approach during transmit is to subdivide the region of interest into a plurality of transmit depths, each using a select group of transmit elements to preserve the insonified area reflecting acoustic energy of a consistent beam profile, thereby maintaining constant tissue volume which is insonified on transmit and constant tissue volume in the focal area on receive.

The number of rings in the array may be determined by the desired number of focal regions or range of focus, each focal region associated with a constant F. In one example of the invention, the F# is maintained constant through the imaging depth by increasing the number of rings linearly with depth. For medical imaging, the desired range of F# is between 1.5 and 3. In one example of the invention, the focal region length F#=2 is approximately 3 mm for 5 MHz, F#=2 operation. Thus, the number of focal regions and rings is the maximum depth divided by 3 mm. For a maximum imaging depth of 90 mm, this gives rise to 30 focal regions and 30 annular array rings. Note that the innermost ring 230-1 is a disc, while the other elements 230-2 through 230-*n* are annular rings which surround the inner disc 230-1.

The width of each ring is determined by the maximum radius of the annular array 211 of FIG. 2A divided by the number of rings n. The diameter of the annular array 210-1 is determined by the maximum depth of imaging divided by the F. An example maximum depth of 90 mm and an F# of 2 results in a maximum diameter of 45 mm and radius of 22.5 mm. The number of rings is determined by the acceptable level of extraneous sidelobes at the focal plane. The wider the rings, the greater this sidelobe level. To be free of extraneous sidelobes would require that each ring be less than ½ the acoustic wavelength, which would result in an unacceptable number of rings. Therefore, in some embodiments, an extraneous sidelobe level between −60 dB and −80 dB of the peak is acceptable (for example −70 dB). At this level, 64 rings are acceptable for a F# of 2, 5 Mhz array with a maximum focus of 90 mm. Such an annular array of radius 22.5 mm and 64 rings gives rise to a ring width of 0.35 mm. (approximately 1 acoustic wavelength in water at 5 MHz).

In certain examples of the invention, it may be desired to image as close to the chest wall as possible. For these applications, a split transducer 210-2 shown in FIG. 2B may be used in that position, where the semicircular part of the transducer faces downward to provide the additional clearance to the chest. In an example where a support 208 or 212 has a vertical array of transducers attached, the semi-circular annular array of FIG. 2B is the top most transducer followed by the circular aperture annular arrays of FIG. 2A, whose axis is placed ½ diameter below the semi-circular annular array. In operation, the semi-circular annular array is used only in that region ½ diameter of that array below the tank for clearance purposes to get as close to the chest wall as possible.

Array Lens

Figure 4:
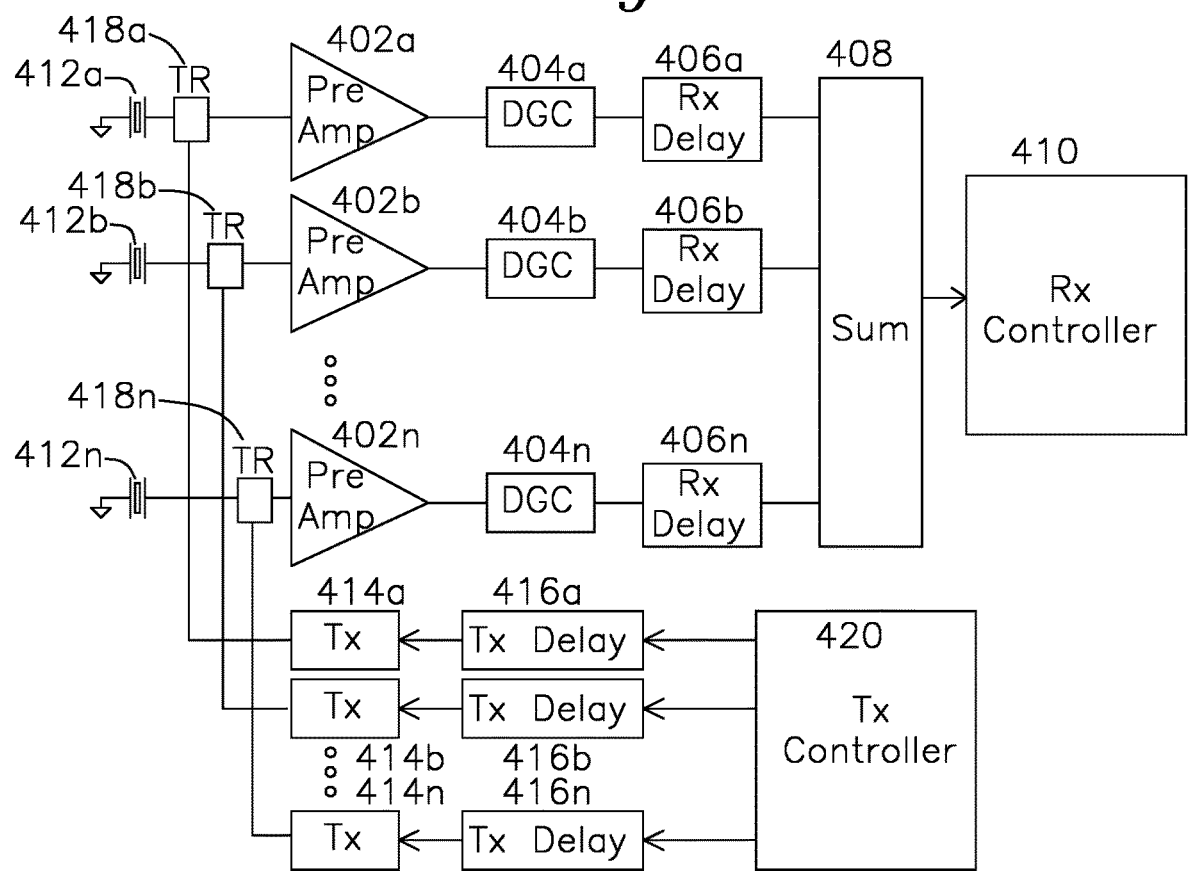
FIG. 4 shows a block diagram of a signal processor for an array imaging system.

Simulations of the annular array shows that 64 rings (63 rings and center disc) gives excellent acoustic performance. An obvious tradeoff exists in system complexity and cost and number of rings, as each ring requires an associated set of electronics in receive chain 402*a*, 404*a*, 406*a*, and transmit chain 414*a* and 416*a*, as shown in FIG. 4. Reducing the number of rings not only makes the annular array less expensive to fabricate, it proportionally reduces the costs of the electronics.

In order to provide a natural range of focus, is typically preferred to provide a concave 234 front surface for the annular array 210-1 of FIG. 2A, and the concave surface may be provided as an acoustic lens attached to the piezoelectric transducer array. In an alternative embodiment shown in FIG. 2D, the annular array piezoelectric element 272 can have a planar front surface and attached to a series of lens elements, each with a different focal length. In this example, the number of annular rings may be reduced with less effects of high extraneous sidelobe level through the use of the Fresnel-like acoustic lens shown in FIG. 2D. Groups of annular ring elements 272-1, 272-2, 272-3, and 272-4 are associated with respective lens elements 270-1, 270-2, 270-3, and 270-4. The construction of the constant F# lens of FIG. 2D is performed by determining the active apertures for each focal zone 265, 267, 269, 271, according to maintaining the ratio of each focal region 265, 267, 269, 271 divided by the respective aperture W (extent over the number of enclosed annular rings) constant. Each lens element 270-1, 270-2, 270-3, and 270-4 has an associated radius of curvature 262, 264, 266, 268 determined by associated focal length 265, 267, 269, 271, respectively. The acoustic lens elements 270-1 through 270-4 focuses acoustic energy from the set of annular rings adjacent to the lens, where the annular rings may operate together as a single channel of FIG. 4, or connected to individual channels of the signal processing diagram of FIG. 4. Each annular ring of transducer 272 is of constant width and focused to a different depth going from inner ring (short focus) to outer (long focus), as shown in the radius of curvature for each lens element associated with 262, 264, 266, and 268. The number of annular rings and their focus can therefore be determined by the annular array and associated system design. The acoustic lens material 270-1 through 270-4 typically has an acoustic velocity less than the acoustic coupling liquid in the liquid bath 106 coupling acoustic energy to the imaged region, and the liquid bath is typically water with a reference acoustic index of refraction of 1. A convex shaped lens will have a positive (converging) focus if the propagating medium (coupling fluid) has a velocity higher than the lens material. Conversely, a concave lens will have a positive focus if the coupling fluid has a velocity that is slower than the lens material.

The rotating transducer arrangement of FIG. 2 presents certain challenges in coupling the signal processing electronics to the transducers. Coupling the transducer array elements external to the rotating assembly would, in its simplest form, require an inordinate number of rotating electrical connections. The needed connections can be significantly reduced by placing the beamforming electronics (FIG. 4) in the rotating assemble and connecting just the received acoustic data and the control signals outside the rotating assembly. In the preferred embodiment, these signals can be connected via a RF link to the rest of the image processing and control circuitry thereby foregoing rotary connections for these signals. Likewise, the electric power for the beamformer can be supplied through an AC or RF field to associated power electronics in the rotating assembly. Such a rotary power connection as well as the associated RF links are in the art of such systems. Such an arrangement as described would completely remove the requirement for rotating electronic connections.

FIG. 3 shows an alternative transducer example of the breast scanner, where the transducers are fixed in position on rings 302 and 304, which eliminates the rotary seal and rotary coupling of electrical signals. Since the size of the acoustic transducer array is much less than the tank dimensions, multiple transducers arrays can be positioned into the rings 302 and 304, shown as 306-1, 306-2, etc. of FIG. 3A.

Alternatively, the transducers may be positioned in vertical arrays (not shown) rather than the circular rings 302, 304.

Other Transducer Assemblies

As described previously, many transducer configurations are possible. The transducers can be arranged in vertical linear arrays on post 208 or 212, the transducers can be positioned at the same or different heights, the transducers may be single and moved axially 202 as shown in FIG. 2, or an array of transducers may be displaced a small displacement on pedestals 208 and 212. The support 206 can be rotated. The annular array transducer providing constant F# can be replaced with other transducer assemblies.

Figure 3:
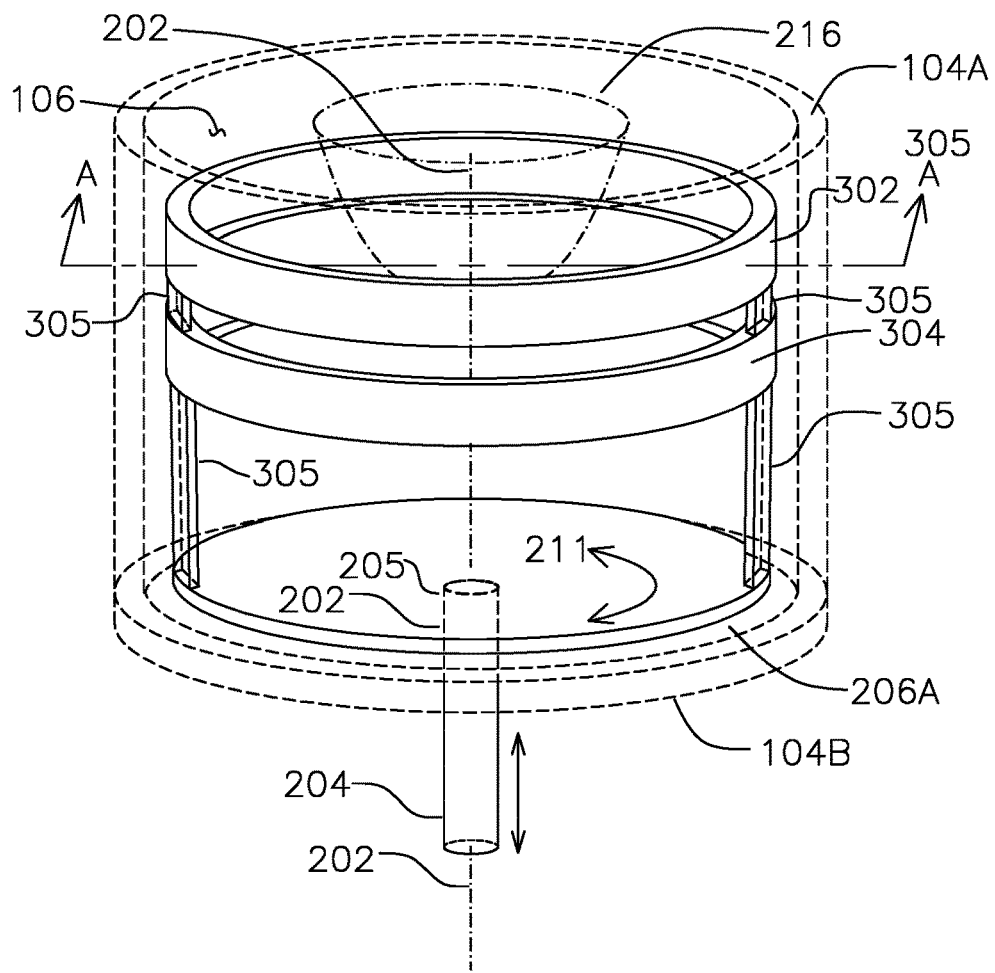
Figure 3A:
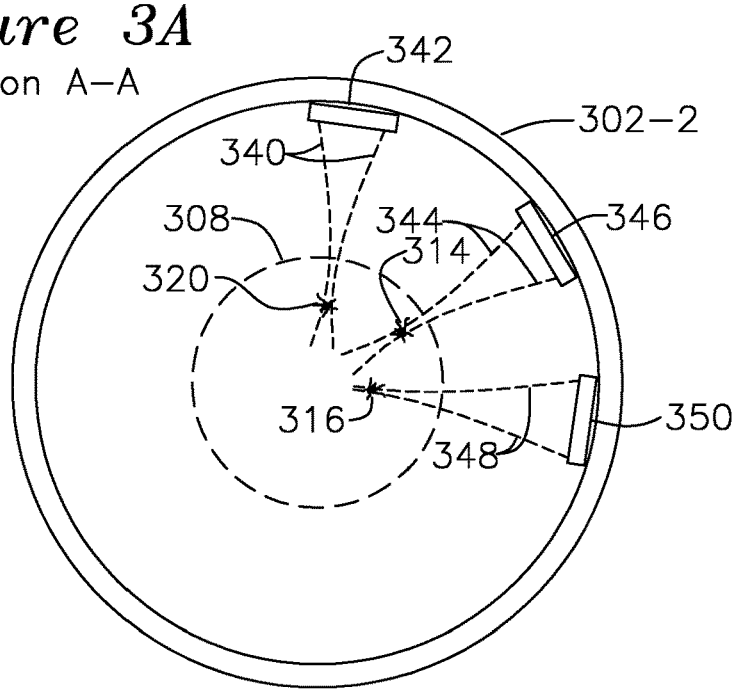
FIG. 3A shows a section A-A for an embodiment of FIG. 3 using discrete transducers.

For example, each annular array of FIG. 2 could be replaced with a circular array arrangement of single focus, fixed F# acoustic transducers as shown in FIGS. 3 and 3A.

In this embodiment, each transducer would have a different focus corresponding to the target set of incremental scan depths, with the number of transducers equal to the number of incremental scan depths for coverage of the entire volume. An example embodiment may include 30 transducers for a scan radius of 3.5" (90 mm). The transmit timing of the transducers can be chosen such that the transmitted acoustic signal of one transducer does not interfere with the received acoustic signal of another. Furthermore, appropriate placement of the transducers in the ring may allow two or more transducers to be utilized in any given transmit/receive cycle to reduce the scan time of a coronal slice.

By placing more such rings of single focus transducers in the vertical dimension (two are shown in FIG. 3, ring 302 and ring 304), the scan time can be proportionally reduced by the number of such transducer rings. This is possible as the translation in the vertical dimension is proportionally reduced as each transducer ring would only need to be moved until its scan plane started to overlap its neighbor. This axial 202 translation could be done while reducing the scan time by spacing the array of transducers a distance M apart from each other, transmitting and receiving at staggered time intervals, and displacing the array of transducers axially 202 in steps of M/r, where r is the individual image slice spacing. To reduce the possibility of the signal from one transducer ring adversely affecting the signal of an another, transmit timing of the transducer rings can be suitably chosen such that the transmitted acoustic signal of each transducer ring does not interfere with the received acoustic signal of the other. Given that only the signal about a small region around each transducer is used, the transducer electronics can be multiplexed between transducers. In one embodiment of the concept, all the transducers can be connected to only one set of electronics thereby greatly reducing cost and complexity.

Figure 3B:
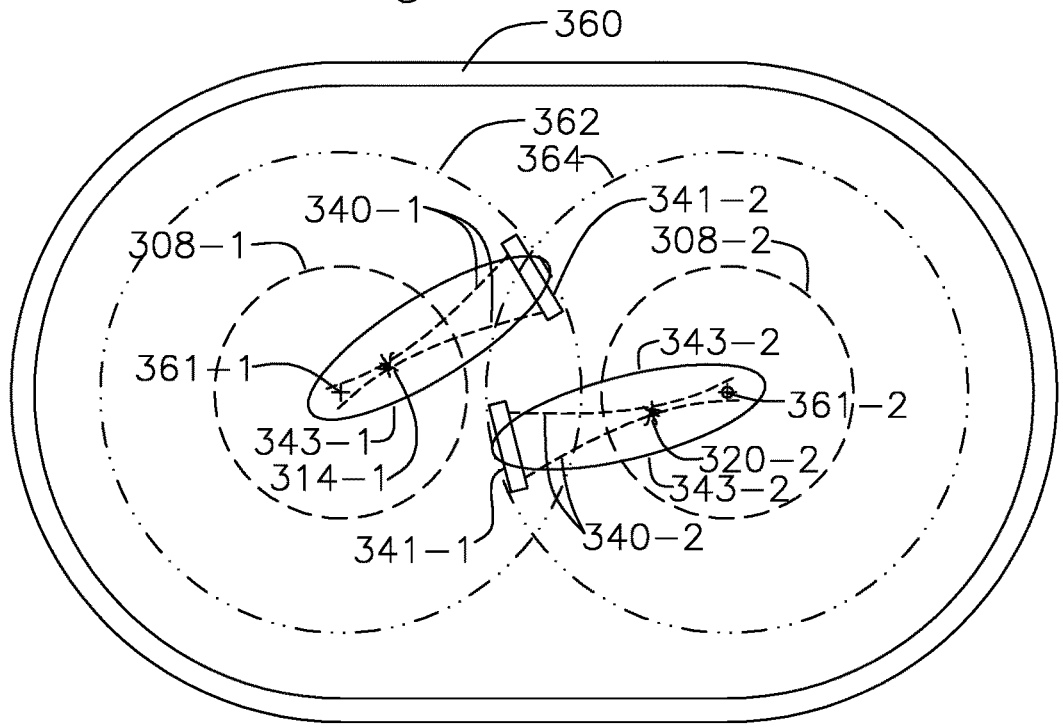
FIG. 3B shows a cross section of a dual scanning embodiment.

FIG. 3B shows an example of the imaging system for simultaneous imaging of both breasts. In this example, the tank wall 360 encloses the couplant for the transducers 341-1 and 341-2, which are mounted on supports 343-1 and 343-2, and rotate about respective axes 361-1 and 361-2. The supports 343-1 and 343-2 rotate in non-interfering directions so that that the respective transducer trajectories 362 and 364 do not mechanically interfere as they image the subject's breast regions 308-1 and 308-2, as shown in example beam plots 340-1 and 340-2. The transducers 341-1 and 341-2 can be any type of transducer and associated translational mechanisms as previously described.

Another example of a transducer assembly is a fixed focus transducer with a focal length of the scan radius and an aperture diameter of half that distance for F#=2 operation. FIG. 2 shows an example where radial position 209 of the focus may be controlled by mechanical motion of the transducer 210 or transducer pedestal 208 along radius 209.

In certain examples of the invention, imaging the breast may also require imaging lymph nodes adjacent to the breast in the axilla, a number of transducers can be added around the tank and positioned upwards to cover these additional outlying areas. These additional transducers would be directed in other angles toward the axilla and may be placed radially away from the axis of rotation, either inside the extent of the outer tank, or on surfaces of table 102 adjacent to the water tank 106. FIG. 2 may be modified to provide additional pedestals 208, 212 and transducers, optionally with radial translation 209 as will be described for FIG. 6.

An example signal processor for the imaging system is shown in FIG. 4. The annular array transducers 412a, 412b, . . . 412n are coupled to corresponding transmit/receive (TR) switches 418a through 418n, one for each annular array ring. On transmit, the transmit controller 420 generates a single, bipolar, or coded transmit pulse, which is individually delayed 416a through 416n for each element, and presented to transmit pulser 414a through 414n and delivered to the piezoelectric transducer ring element via transmit/receive (T/R) switches 418a through 418n. The transmit delay 416a through 416n is optionally provided to allow the transmit beam to be focused on a particular axial region as shown in FIG. 2C (such as transmitting to each focal region in a separate transmit), and the transmit controller 420 selects the number of rings to transmit, such as by expanding the number of transmit elements to create the focal regions 252, 254, and 256 of FIG. 2C. The receive processing of FIG. 4 operates similarly, with preamplifiers 402a through 402n associated with each annular ring, the preamplifier 402a through 402n providing signal to depth gain control amplifiers 404a through 404n compensating for tissue attenuation with depth, and summer 408 may select an increasing number of rings from center to outer to maintain constant F number as described in FIG. 2C, as well as provide apodization to smooth sidelobes as is known for ultrasound signal processing. The receive controller outputs the detected signal and/or the complex analytic signal, and/or the undetected signal representing a single line of reflected acoustic data from the structures along constant 3D spatial resolution imaging range of focus 252, 254, 256 of FIG. 2C, which are individually added with each change in angular position to provide a series of section views such as those shown in FIG. 3A or 3B, with a possible objective of early detection of the spiculated structures 314, 316, 320 as well as other medically relevant structures.

Other Imaging Modalities

In another variation of the invention of FIG. 2, where the two transducers 210 and 214 are positioned at the same height above support 206, and one transducer 214 transmits acoustic waves and the opposing transducer 210 receives acoustic saves after passing through the imaged breast in a modality known as acoustic transmission imaging. In this configuration, two modes are available, one mode for transmission imaging and one mode for reflection imaging. In reflection imaging, the transceiver annular array may transmit a pulse and receive a reflection from acoustic structures within the breast. In transmission imaging and reflection imaging, the transmitting annular array may transmit a pulse and the transceiver array may receive it. In one embodiment, the transmitted pulses are focused to the same region of space as the receiver. In another example of transmission imaging, the pulses may be provided as coded sequences such as for harmonic imaging. In one example of using coded sequences, a pulse sequence is sent followed by an inverse of the same pulse sequence as short time later. In this example, the fundamental frequency components are reduced and the second order components are enhanced due to nonlinearities of propagation in tissue. Other coded sequences are selected which provide enhanced imaging of the elastic properties of tissue.

The scanning pedestals 212 and 208 may support other transducers in addition to the acoustic transducers. In one example of the invention, photoacoustic imaging can be incorporated by adding a laser source to induce an acoustic signal in tissue or blood where the laser light is readily absorbed. In this example, it may be preferred to provide an aperture in the central disc of the annular array for the inclusion of axial laser energy, thereby illuminating the line of acoustic foci of the annular array. The transducer arrangements may be varied. Considering the z axis to be perpendicular to the face of the transducer, the fixed F# annular array is able to provide fixed beam cross section profile in z by virtue of circular symmetry, and so is translated in x and y for acquisition of adjacent constant 3D spatial resolution regions. A linear array, where groups of elements are stepped linearly along x, can provide a fixed cross section profile at a particular depth z, but the use of this type of transducer requires the transducer be mechanically moved in the z direction to ensure constant 3D spatial resolution regions acquisition occurs, and in the y direction to image adjacent voxels of the region of interest.

Alternatively, X-Ray imaging could also be added to the pedestals 208 and 212, or outside the extent of the enclosure 104A. For use inside the enclosure 104A, a small collimated X-ray sources having a collimated beam the same diameter as the desired resolution can be used, with an x-ray detector positioned opposite from the X-ray source. The x-ray source and x-ray detector can be positioned adjacent to the acoustic transducers, preferably to the side so that the image plane of the X-ray image would be in the same plane as the acoustic image.

In another example of the invention, microwave imaging could also be added to provide additional imaging information. Specifically, using focused microwave antennas in the same way as the acoustic arrays, the microwave energy could be transmitted and received in a manner like that of the acoustic imaging already described. In some embodiments, the system may operate analogous to a traditional radar. Also, like its acoustic counterpart, co-axial opposite antennas may be used to produce microwave transmission images.

As can be seen from the preceding examples, a key advantage of the scanning mechanism is its ability to incorporate other breast imaging modalities thereby producing simultaneous and registered clinically relevant breast images.

Replaceable Inner Water-Bath

Figure 5:
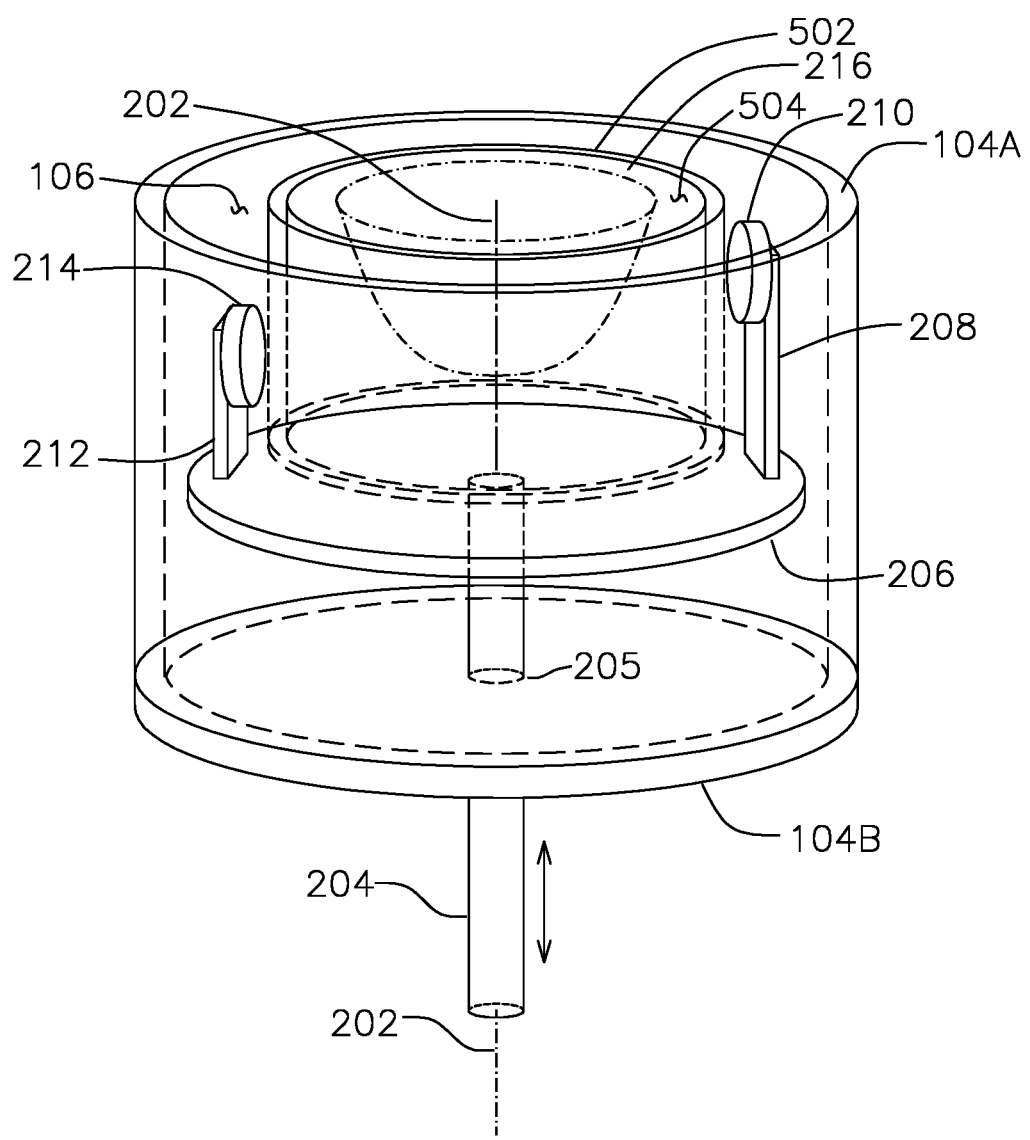
FIG. 5 shows a perspective view of a dual containment system.

One of the problems with water-bath based imaging systems is the need to clean and, possibly, sterilize the water tank between patient uses. FIG. 5 shows an example of the invention with separate water bath having an inner tank wall 502 thickness no more than 10% greater than, and no less than, the axial spatial resolution increment of the system. Alternatively, the wall thickness may be less than ¼ a wavelength of propagating ultrasound energy. Cylindrical inner tank 502 and cylindrical outer tank 104A are shown for simplicity and understanding the invention. In other examples of the invention, the inner tank 502 is a form-fitting acoustically transparent surface which accommodates both breasts to be imaged. Inner enclosure 502 can be added to the structures of FIG. 2, thereby creating an inner fluidic bath 504 and outer fluidic bath 106. Inner enclosure 502 may be separately disposable, or alternatively, inner enclosure 502 can be removable and easily cleaned and sanitized. In other examples of the invention, inner enclosure 502 may be added to the embodiment of FIG. 3. In the embodiments with a removable inner enclosure 502, the outer bath 106 contains the transducer assembly and the inner bath 504 contains the patient's breast to be imaged. The inner bath 504 tank 502 is either a consumable, or a tank that can be cleaned and sterilized by the customer through standard medical means and filled with sterile and degassed couplant, such as water, provided by the customer. In another example embodiment, the inner tank 502 is a disposable one-time use tank. It should be noted that water may not be the best acoustic interface between the imaging system and the breast. For medical and/or operational reasons, other fluids to be used as couplants can be considered.

In traditional imaging systems, the container 502 for the inner bath can cause imaging artifacts (echoes and distortions) due to reflections between the transducer and the bath tank wall and/or multiple reflections within the tank wall. In one reflection minimizing construction, the inner tank wall 502 can be selected with a thickness such that the acoustic reflections of the acoustic signals from the sample time range occur outside the sample time range. This can be accomplished with a wall thickness no more than 10% greater than, and no less than, the axial spatial resolution increment of the system. Thus, the triple transit reflection from tank wall 502 of the sample time range cannot result in an echo as it will occur later than the sample time range. However, triple transit reflections of acoustic signals originating before the sample time range will result in image artifacts (echoes). The straight path of these earlier acoustic signals (i.e. not reflected) will occur a known time before the acoustic signal in the sample time range. Sampling this earlier set of signals provides the information to significantly reduce the echo artifacts in the sample time range using echo cancellation methods known in the art. The same can be true for the reflection between the inner bath tank wall and the transducer. That said, this distance could be so large that significant turbulence is generated between the rotating transducer assembly and the inner tank wall. This turbulence and resulting hydrodynamic drag of the interaction between the fluid 106 and moving pedestal/transducers 208/210 and 212/214 can be significantly reduced by reducing the distance between the inner bath tank wall 502 and the rotating transducer assembly 210/214. This, unfortunately, could result in imaging artifacts occurring within the image time range but can be reduced by echo cancellation methods known in the art. Finally, the acoustic impedance of the transducer and inner tank wall 502 can be closely matched to the acoustic fluids 106 and 504 such that there are minimal reflections, subject to the limitations of existing materials and index of refraction matching.

To reduce the image artifacts due to a small distance between the transducer assembly and the inner tank wall, there are a number of solutions. One example of the invention is to match the acoustic impedance (to less than 10% difference) of the fluid between the transducer assembly 210/214 and inner tank wall 502 to that of the transducer 210/214 and the inner tank wall 502. The resulting reflection between the inner tank wall and the water in the inner tank bath would fall outside the time gated range of the image data. Another solution would be to reduce the distance to wall thickness no more than 10% greater than, and no less than, the axial spatial resolution increment of the system. Yet another solution would be to make the distance between the transducer assembly 210/214 and the inner tank wall 502 so thin (less than ¼ the propagating acoustic wavelength) as to effectively remove the effects of triple transit between the two even if there is an appreciable mismatch between the transducer 210/214, fluid 106, and tank wall 502. Even in this case, however, the acoustic impedance of the transducer 210/214 and the inner tank wall 502 should be close enough to allow for significant (greater than 50% of the acoustic energy) transmission of sound through this interface. Another issue with the short distance between the transducer assembly 210/214 and the inner tank wall 502 is the precision required in the diameter of the inner tank wall as well as its positioning in the exact center of the transducer scanning mechanism.

The inner tank 502 can cause unwanted distortion of the acoustic beam focus. This is particularly true if the acoustic couplant 504 in the inner tank has a different speed of sound than the acoustic couplant 106 between the transducers and the inner tank. For a cylindrical inner tank 502, the resultant cylindrical distorting of the focus can be corrected by adding an opposing cylindrical distortion to the native focus of the transducers 210/214. This can be achieved by placing a suitable cylindrical lens in front of each transducer to predistort the beamform in a manner which is the inverse of the distortion caused by the tank wall 502. Another solution would be to add a suitable cylindrical curvature to each transducer to achieve the same effects as the lens.

Figure 6:
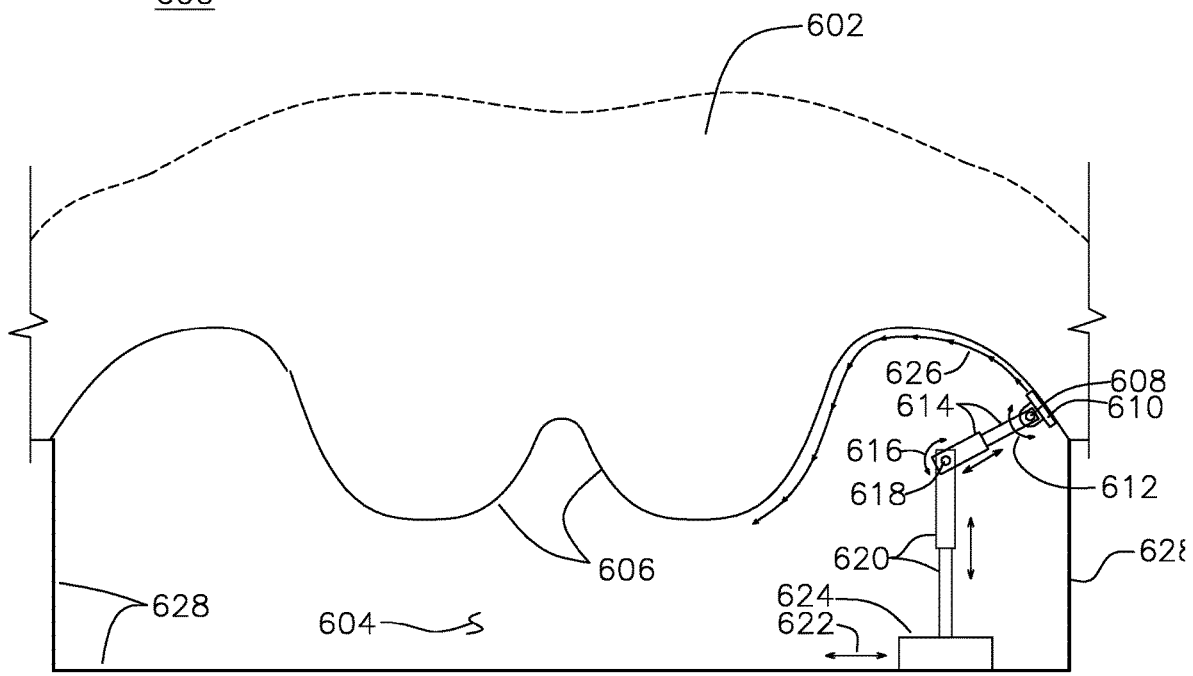
FIG. 6 shows a cross section view of an embodiment of the invention for additionally scanning regions adjacent to a human breast.

Another variation in tank design 600 for imaging the axilla regions of subject 602 is shown in FIG. 6, which is a cross section view of a subject 602 to be imaged using example transducer 610 which pivots on first extensible member 614 with pivot mount 618 to second extensible member 620 which is mounted to a translatable base 624, which may translate laterally 622 as shown, or from a superior to an inferior anatomical position (perpendicular to the plane of the figure), or in any direction or orientation which provides access to the region to be imaged. The degrees of freedom include translation 622, rotation 616 and 612, and extensions of 614 and 620, which allow the transducer 610 to follow trajectory 626 to image axilla and optionally breast areas of subject 602. The tank is bounded by walls and bottom 628 and acoustically transparent membrane or plate 606 which provides acoustic transducer 610 imaging access to subject 602. The acoustically transparent membrane or plate 606 may be any rigid or conformable material which provides access for moveable transducer 610, which may be moved along the path 626 shown for imaging lymph nodes adjacent to the breast. Many mechanisms are available which provide the capability for transducer 610 to move along path 626, for which one example is given. The transducer configuration for scanning breasts 608 are not shown, but may be any of the previously described imaging structures without limitation, and may also be combined with the double enclosure of FIG. 5.

Figure 6A:
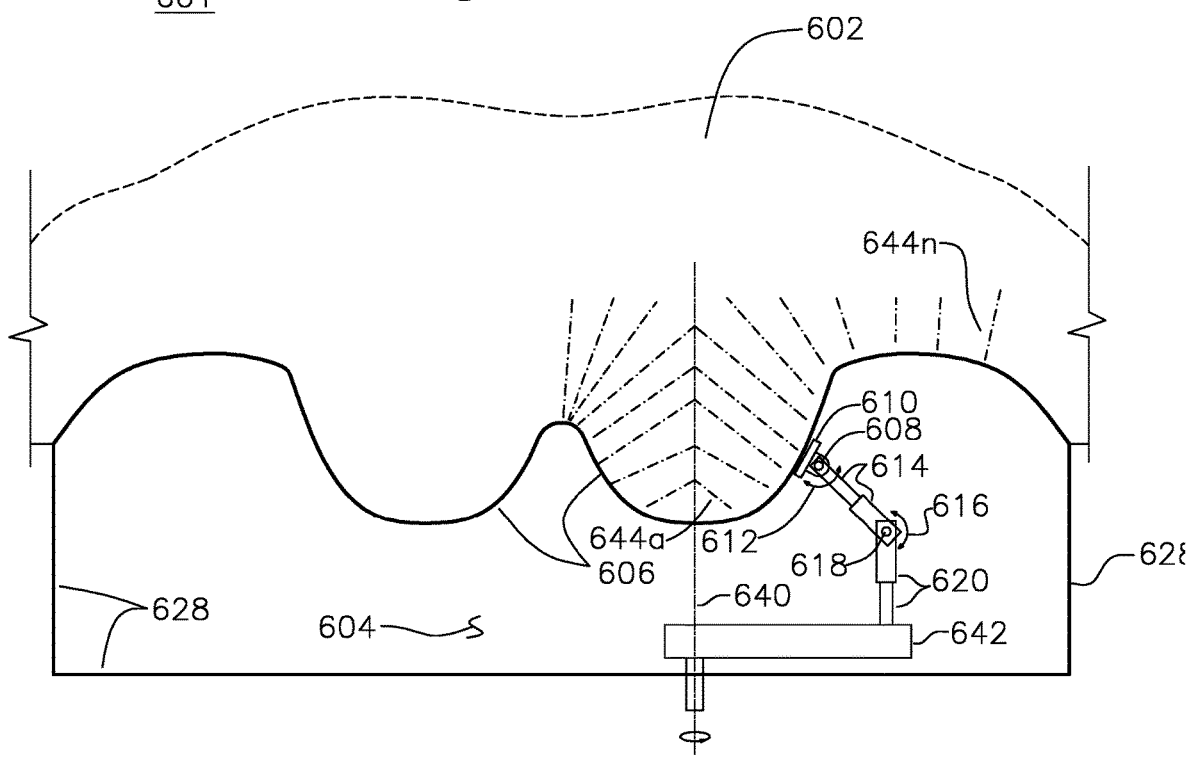
FIG. 6A shows an example of the breast scanner for use with a conformable or rigid acoustically transparent surface.

FIG. 6A shows a variation of FIG. 6, where the transducer arm 620 is attached to a rotatable support 620, such that the transducer arm 620 and associated mechanisms such as those of FIG. 6 couple rotation of transducer 610 rotate about a center of the breast to be imaged, where the breast is positioned by a rigid or semi-flexible acoustically transparent form 606. The transducer is thereby able to circumnavigate the breast to be imaged to generate a series of 3D spatial resolution regions along image planes 644a through 644n. The acoustic data from the planes can then be used to create 3D image data set of constant sized voxels. From this dataset, 2D image slices of any orientation can be created. A second rotatable arm assembly may optionally be positioned to scan the other breast, although just one mechanism is shown for clarity and understanding the invention. The rotation of transducer support 642 and articulation of rotatable joints 612 and 618, and variable length arms 614 and 620 may be performed separately or together, such that the transducer may rotate about the breast as shown in FIG. 6A and the rotation of support 642 stopped to allow the transducer to follow a plurality of paths such as 626 for most general operation, such as for acquiring constant dimension voxels for imaging the axilla before or after the breast is imaged using the constant 3D spatial resolution acquisition techniques described.

Correction for Patient Movement

Patient motion over the 3+ minute scan is certainly possible in practice. During operation, processing the various imaged scans can be aligned using the imaged surface of the breast as a template. Movement during a slice scan is more problematic to correct but easy to detect via a secondary pulse/echo acoustic submodule that looks for breast surface motion during scanning. Correcting for motion artifact in the acquired data can be accomplished by using topological matching techniques by translating features until they align on adjacent image slices. An additional method to correct for motion during a slice scan is to repeat the scan if motion is detected. It is expected that such correction may add only, on average, 10 seconds to the overall 3D breast imaging cycle.

Image Acquisition and Analysis Based on Image Templates Used with Artificial Intelligence In the example of FIG. 3A, cross sectional images showing characteristic lesions such as spiculated masses 320, 314, 316, which are distinguishable as echoic masses with tendrils extending from the spiculated mass or microcalcifications, a collection of small bright spots in a cystic region or mass. Lesions such as the spiculated and calcified masses may be detected through the comparison of the acquired image with a series of template images for use with a computer algorithm and correlation score, with the correlation score provided as a match metric to the characteristics of the tendril template according to tendril length to diameter or other metrics.

Additionally, Artificial Intelligence (AI) may be used in detection of masses or for high resolution examination of subregions of acquired images through supervised or unsupervised learning. For example, a constant 3D spatial resolution and constant voxel size 3D images or constant pixel size images may be coupled with AI in the determination of breast disease. Using any imaging technology with AI to determine disease requires a large learning data set of annotated images to teach the AI system to recognize a specific disease state. The more variable the resolution and pixel or voxel size of the images, the more learning images are required to achieve a certain accuracy. The number can easily reach into the 100s of thousands. The constant 3D spatial resolution of the disclosed technology greatly reduces the required number, potentially into the thousands. This is an advantage as annotated images are time consuming and very expensive to create. Thus, the use of AI with the disclosed technology leads to faster time to market and lower costs.

Within the disclosed technology, AI can be used to improve the acoustic signal quality, correct for distortions due to systematic errors and patient movement, and reduce the operator's workload. Improvement of the acoustic signal can be achieved by teaching an AI subsystem to dynamically correct for variations in the acoustic signal due to physical processes such as absorption and non-linear acoustic propagation that are patient dependent. Image distortions can be introduced through fabrication errors in the system. The AI subsystem can be "taught" to correct for those distortions at the factory or through a calibration cycle at the point of use. An AI subsystem can also be used to correct for patient motion. Though other algorithmic subsystems will be used, specifically those using sensors to monitor the movement of the breast, an AI subsystem can be used to correct for those movement errors that are not easily corrected by algorithmic means. An AI system can be used to dynamically learn an operator's work practice and offer suggestions to reduce the operator's workload. For example, the AI system could monitor the time and sequence of procedures of the operator's interaction with the patient and offer different sequence of events such as which breast to image first thereby reducing the patient time with the imaging system and operator workload.

In the present application, "approximately" or "substantially" is understood to mean a variation of +/−50% of the nominal value for a linear dimension, +/−30 degrees for an angle, or +/−3 dB for a signal level. "On the order of" is understood to be in the range of 1/10th of the nominal value to 10× the nominal value, and a material which is "acoustically transparent" is a material which has an attenuation of less than 50% of the acoustic energy. Furthermore, constant size and resolution, or substantially uniform spatial resolution volume is understood to be a voxel or pixel size or 3D or 2D spatial resolution of an area returning ultrasound signal that is no more than 50% larger than each dimension of an adjacent spatial resolution volume, voxel, or pixel size. The present examples are provided for illustrative purposes only, and are not intended to limit the invention to only the embodiments shown. While illustrative embodiments have been illustrated and described, it will be appreciated that various changes can be made therein without departing from the spirit and scope of the invention.

I claim:

1. An ultrasound scanning system comprising:
an enclosure for an acoustic couplant;
at least one ultrasound scanning mechanism, each said ultrasound scanning mechanism comprising:
  a shaft rotatable about an axis, the shaft coupled to a first support;
  the first support coupled to a second support, the second support coupled to an ultrasound transducer and providing an adjustable offset from the first support;
  the ultrasound transducer transmitting acoustic energy and receiving reflected acoustic energy, the received acoustic energy representing acoustic reflections from a volume of tissue to be imaged;
  a receiver coupled to the ultrasound transducer, the receiver operative to receive acoustic reflections from a plurality of substantially uniform sub-volumes of tissue over the volume of tissue;
  the ultrasound transducer maintaining a fixed F# to receive acoustic reflections from each substantially uniform sub-volume of tissue by changing a length of the adjustable offset for each substantially uniform sub-volume of tissue of the plurality of substantially uniform sub-volumes of tissue which are providing reflections, while maintaining the fixed F# for each receive acoustic reflection.

2. An ultrasound scanning system comprising:
an enclosure for an acoustic couplant;
at least one ultrasound scanning mechanism, each said ultrasound scanning mechanism comprising:
  a shaft rotatable about an axis, the shaft coupled to a first support;
  the first support coupled to a second support substantially perpendicular to the first support, the second support coupled to an ultrasound transducer and providing an adjustable offset from the first support, the ultrasound transducer comprising a plurality of transducer elements;
  a beamformer coupled to the ultrasound transducer, the beamformer generating regions of transmit focus and regions of receive focus within each region of transmit focus during separate intervals by delaying signals to and/or from the transducer elements;
  the ultrasound transducer transmitting acoustic energy and receiving reflected acoustic energy, the received acoustic energy representing acoustic reflections from a volume of tissue to be imaged, the beamformer operative to enable the transducer elements to receive reflections from a plurality of substantially uniform sub-volumes of tissue from the volume of tissue to be imaged, the beamformer also configured to maintain a constant F#;
  the ultrasound transducer operative to receive acoustic reflections from the plurality of substantially uniform sub-volumes of tissue over the volume of tissue, the uniform sub-volumes of tissue including uniform sub-volumes of tissue at a fixed focal length of the transducer;
  the ultrasound transducer adjustable offset modified to place a focal length of the transducer at each substantially uniform sub-volume of tissue.

3. The ultrasound scanning system of claim 2 where delaying signals to and/or from the transducer elements comprises electronic delay elements and also a plurality of concentric lens segments arranged about a central axis of the ultrasound transducer, each concentric lens segment coupled to a planar surface of the ultrasound transducer, each concentric lens segment having a first lens surface in contact with the ultrasound transducer planar surface and a second lens surface opposite the first lens surface with a radius of curvature located on the central axis, each radius of curvature of an associated concentric lens segment increasing monotonically from an inner concentric lens segment to an outer concentric lens segment.

* * * * *